(12) United States Patent
Mohammadi

(10) Patent No.: US 6,264,964 B1
(45) Date of Patent: Jul. 24, 2001

(54) FOAMING COSMETIC PRODUCTS

(75) Inventor: Fatemeh Mohammadi, Hebron, CT (US)

(73) Assignee: Conopco, Inc., New York, NY (US)

( * ) Notice: Subject to any disclaimer, the term of this patent is extended or adjusted under 35 U.S.C. 154(b) by 0 days.

(21) Appl. No.: 09/436,117

(22) Filed: Nov. 8, 1999

Related U.S. Application Data

(60) Provisional application No. 60/129,273, filed on Apr. 14, 1999.

(51) Int. Cl.$^7$ .......................................... A61K 7/00
(52) U.S. Cl. .................. 424/401; 424/47; 424/78.03; 424/486; 514/844
(58) Field of Search ................. 424/47, 78.03, 424/401, 486; 514/844

(56) References Cited

U.S. PATENT DOCUMENTS

| | | |
|---|---|---|
| 4,022,351 | 5/1977 | Wright . |
| 5,364,031 | * 11/1994 | Taniguchi et al. . |
| 5,833,973 | 11/1998 | Dobkowski et al. . |

FOREIGN PATENT DOCUMENTS

| | | |
|---|---|---|
| 0 240 349 | 4/1987 | (EP) . |
| 11193214 | 7/1999 | (JP) . |
| 97/32561 | 9/1997 | (WO) . |
| 97/44010 | 11/1997 | (WO) . |
| 98/00103 | 1/1998 | (WO) . |

OTHER PUBLICATIONS

IFSCC International Congress Yokohama, Oct. 13–15, 1992; pp. 289–296.
International Search Report.

* cited by examiner

*Primary Examiner*—Francisco Prats
*Assistant Examiner*—Susan D. Coe
(74) *Attorney, Agent, or Firm*—Milton L. Honig

(57) ABSTRACT

A foaming cosmetic product is provided which is packaged within a container fitted with pump and nozzle to express a cosmetic composition in mousse form. Foam may be generated by an agent which is a mechanical device such as a screen within a valve or by an aerosol propellant in a pressurized system. The cosmetic composition includes a crosslinked non-emulsifying polysiloxane elastomer and a carboxyvinyl polymer, the latter stabilizing the composition against separation and contributing to a rich dense foam.

7 Claims, No Drawings

US 6,264,964 B1

FOAMING COSMETIC PRODUCTS

This application claims benefit of Provisional No. 60/129,273 filed Apr. 14, 1999.

BACKGROUND OF THE INVENTION

1. Field of the Invention

The invention concerns foamed cosmetic compositions generated by aerosol or mechanical pump action.

2. The Related Art

Foam quality of product expressed in mousse form may be greatly affected by the formulation components. For instance, many silicone compounds are anti-foam agents. Collapse or at least poor quality foam often results from inclusion of silicone compounds. Yet in the area of cosmetic chemistry, silicone compounds have highly beneficial skin-feel and other properties.

Crosslinked non-emulsifying siloxane elastomers have been reported as being excellent cosmetic ingredients. For instance, U.S. Pat. No. 5,833,973 (Dobkowski et al.) describes inclusion of siloxane elastomer into an aqueous emulsion to achieve improved skinfeel properties.

WO 97/32561 (Nawaz) describes skincare compositions including a crosslinked polyorganosiloxane polymer, silicone oil, organic liquid crystal-forming amphiphilic surfactant and water to form an oil-in-water emulsion. Gelling agents such as carboxyvinyl polymers are optional further components. These compositions are reported to improve skinfeel, reduce greasiness/stickiness and have faster absorption.

A poster presentation at the IFSCC International Congress in Yokohama in 1992 (pages 289–296) presented by Sakuta described the usefulness of crosslinked silicone polymers as thickening agents for dimethylpolysiloxane. Stable water-in-oil emulsions were reported to be obtainable by using a polyoxyalkylene-modified silicone oil. A cosmetic foundation was described wherein a Carbomer was formulated along with the silicone elastomer and various pigments.

Although the art has recognized the usefulness of silicone elastomers in skin cosmetics, there has been no description of formulations successfully incorporating this substance into mousse type products. Formulation of mousses presents many challenges. These include the problems of providing rich and stable foams, avoidance of nozzle cloggage, storage stability of concentrates and good skinfeel of the resultant foamed product.

Accordingly, it is an object of the present invention to provide a cosmetic composition in mousse form having a rich long-lasting foam and good skinfeel.

Another object of the present invention is to provide a cosmetic composition in mousse form which has good physical stability.

These and other objects of the present invention will become more readily apparent from consideration of the following summary and detailed description.

SUMMARY OF THE INVENTION

A foaming cosmetic product is provided which includes:
(A) a container with a nozzle outlet and a foaming mechanism; and
(B) a cosmetic composition including:
  (i) from about 0.001 to about 2% by weight of a crosslinked carboxyvinyl polymer;
  (ii) from about 0.1 to about 30% of a crosslinked non-emulsifying siloxane elastomer; and
  (iii) from about 1 to about 80% of a volatile polyorganosiloxane.

DETAILED DESCRIPTION OF THE INVENTION

Now it has been found that mousse products incorporating crosslinked non-emulsifying siloxane elastomers can be elegantly delivered through a pump mechanism with the assistance of a crosslinked carboxyvinyl polymer. Systems for this invention are aqueous emulsions, particularly oil-in-water emulsions.

Crosslinked non-emulsifying siloxane elastomers are a first essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si—H linkages of a polysiloxane backbone such as a molecularly spherical MQ resin. Elastomer compositions are commercially available from the General Electric Company under product designation General Electric Silicone 1229 with CTFA name of Cyclomethicone and Vinyl Dimethicone/Methicone Cross Polymer, delivered as 20–35% elastomer in a cyclomethicone carrier. A related elastomer composition under the CFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries may be further processed by subjecting them to a high pressure (approximately 5,000 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar. 60 rpm. 15 sec.).

Amounts of the elastomer may range from about 0.1 to about 30%, optimally from about 1 to about 15%, most preferably from about 3 to about 10% by weight.

A second element of the present invention is that of a volatile polyorganosiloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxane containing from about 3 to about 9 silicone atoms. The linear volatile silicones generally have viscosities of less then about 5 centistokes at 25° C., while the cyclic materials have viscosities of less than about 10 centistokes, the preferable range being from 0.1 to 8 centistokes. Examples of silicone oils useful in the present invention include: Dow Corning 224, Dow Corning 245, Dow Corning 344, Dow Corning 345 and Dow Coming 200 (manufactured by the Dow Corning Corporation); Silicone 7207 and Silicone 7158 (manufactured by the Union Carbide Corporation); SF1202 (manufactured by General Electric).

Amounts of the volatile polyorganosiloxane will range from about 1 to about 80%, preferably from about 20 to about 70%, optimally from about 30 to about 65% by weight.

A most important element of the present invention is that of a carboxyvinyl polymer. Most preferred are polymers known in the technology as Carbomers. These resins are essentially colloidally water-soluble polyalkenyl polyether polymers of acrylic acid crosslinked with from 0.75 to 2% of polyallyl sucrose or polyallyl pentaerythritol. Carbomers are available from the B.F. Goodrich Company under the trademark Carbopol. Examples include Carbopol 934, Carbopol 940, Carbopol 980, Carbopol 1382, Carbopol 1342 and Pemulen TR-1 (CTFA designation: Acrylates/10/30 Alkyl Acrylate Crosspolymer). Particularly preferred is a 2% active aqueous solution of Carbopol 1382. Amounts of the carboxyvinyl polymer on an active basis may range from about 0.001 to about 2%, preferably from about 0.01 to about 1%, more preferably from about 0.3 to about 0.8% by weight.

Cosmetic compositions of the present invention are aqueous emulsions. Amounts of water may range from about 30 to about 85%, preferably from about 55 to about 70% by weight. The emulsions may be of the oil-in-water, water-in-oil or duplex variety. Most especially, the invention is concerned with the oil-in-water variety.

Aqueous to oily phases will range in weight from about 10:1 to about 1:10, preferably from about 1:1 to about 2:1, optimally from about 1:1 to about 1.5:1.

Surfactants may be a further component of compositions according to the present invention. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids and sorbitan. These materials are available, for instance, from the Shell Chemical Company under the Neodol trademark. Copolymers of polyoxypropylenepolyoxyethylene sold by the BASF Corporation under the Pluronic trademark are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates, sarcosinates, taurates and sodium fatty acyl isethionate.

Amphoteric surfactants include such materials as dialkylamine oxide and various types of betaines (such as cocamidopropyl betaine).

Most advantageously the surfactant or emulsifier system is a combination of a glyceryl fatty acid ester such as glyceryl stearate in combination with an alkyl phosphate such as cetyl phosphate (available as Amphisol® A sold by the Givaudan Corporation). Preferred amounts of each of these materials may range from about 0.1 to about 5%, optimally from about 0.8 to about 2.5% by weight.

Compositions of the invention may optionally contain a skin conditioning agent. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,2-butylene glycol, 1,2,5-hexanetriol, ethoxylated glycerin, propoxylated glycerin and mixtures thereof. Most preferably the humectant is glycerin. Amounts of humectant may range anywhere from about 1 to about 50%, preferably from about 10 to about 40%, optimally from about 25 to about 25% by weight.

Exfoliants according to the present invention may be selected from alpha-hydroxycarboxylic acids, beta-hydroxycarboxylic acids and salts of these acids. Most preferred are glycolic, lactic and salicylic acids and their ammonium, potassium or sodium salts.

When the conditioning agent is an emollient it may be selected from hydrocarbons, fatty acids, fatty alcohols and esters. Petrolatum is the most preferred hydrocarbons type of emollient conditioning agent. Other hydrocarbons that may be employed include mineral oil, polyolefins such as polydecene, and paraffins such as isohexadecane (e.g. Permethyl 99® and Permethyl 101®).

Fatty acids and alcohols will have from 10 to 30 carbon atoms. Illustrative of this category are pelargonic, lauric, myristic, palmitic, stearic, isostearic, hydroxystearic, oleic, linoleic, ridnoleic, arachidic, behenic and erucic acids and alcohols. Ester emollients based on the fatty acids, polyalkoxylated derivatives of the fatty acids or alcohols and combinations thereof may also be useful. Vegetable derived ester can be similarly effective. Examples include soybean oil, cottonseed oil and maleated soybean oil.

Amounts of the skin conditioning agent may range from about 1 to about 50%, preferably from about 3 to about 25%, optimally from about 5 to about 20% by weight.

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are alkyl esters of parahydroxybenzoic add. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

A further essential element of foaming cosmetic products according to the present invention is a foaming mechanism. This mechanism may be in the form of a mechanical device or it can be an aerosol propellant. When it is a mechanical device it will be employed with a non-aerosol dispenser. Illustrative is a dispenser characterized by a container for storing the cosmetic composition, a dispensing head defined by a housing containing a pump, and a diptube for transferring the composition from the container into the dispensing head. Foam is created by requiring the composition to pass through a screen material which may be a porous substance such as a sintered material, a wire (plastic or metal) gauze screen or similar structures.

Suitable dispensers are described in U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.) and U.S. Pat. No. 5,364,031 (Tamiguchi et al.). Most preferred however is a device sold by the Airspray International Corporation described in WO 97/13585 (Van der Heijde). All these patents are incorporated herein by reference. The Airspray device comprises a container for storing a cleansing composition and dispensing head, the latter including at least a concentric air pump and liquid pump. Each of the pumps has a piston chamber with a piston displaceable therein and an inlet and discharge, and an operating component for operating the two pumps. The operating component is integral with one of the pistons and comprises an outflow channel with a dispensing opening. Shut-off mechanisms, rendering it possible to suck up air or liquid, respectively, and dispense them, are present in the inlet and discharge of the pumps. The air pump includes a double-acting shut-off device which can be operated actively by the operating component. The shut-off device prevents both the inlet of air to the pump and discharge of air therefrom. The air piston is able to be moved freely at least over a small distance with respect to the operating component.

Aerosol propellants in pressurized metal cans or in suitable bottles may also be employed as a foam mechanism. Propellants which may be used include $C_1$–$C_6$ alkyl ethers, $C_3$–$C_6$ hydrocarbons, halocarbons, carbon dioxide and mixtures thereof. Illustrative hydrocarbons include n-butane, isobutane, isobutane/propane mixtures all of which are available from the Phillips Petroleum Company under the respective trademarks A17, A31, A46 and A70. Among the alkyl ethers, more prominent is dimethyl ether, diethyl ether, methyl ether ether and diisopropyl ether. Most preferred is dimethyl ether. Halocarbons can include dichlorodifluoromethane, dichlorotetrafluoroethane, chlorotrifluoromethane and mixtures thereof. Amounts of propellant may range from about 1 to about 40%, preferably from about 2 to about 15%, optimally between about 3 and about 12% by weight based on the cosmetic composition and propellant combination. Nozzles for the aerosols may be regulated by valves such as those available from the Precsion Valve Company.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–10

The following formulations illustrate cosmetic compositions which are incorporated into a non-aerosol pump with a nozzle communication with an Airspray Company screen foaming device.

TABLE I

| COMPONENT | EXAMPLE (WEIGHT %) | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| PHASE A | | | | | | | | | | |
| Carbopol 1382 ® (2% Active) | 5.0 | 5.0 | 10.0 | 10.0 | 1.0 | 1.0 | 1.0 | 5.0 | 5.0 | 15.0 |
| Disodium EDTA | 0.1 | 0.1 | 0.1 | 0.1 | 0.1 | 0.1 | 0.1 | 0.1 | 0.1 | 0.1 |
| Butylene Glycol | 1.7 | 1.7 | 1.7 | 1.7 | 1.7 | 1.7 | 1.7 | 1.7 | 1.7 | 1.7 |
| Glycerin | 1.9 | 1.9 | 1.9 | 1.9 | 1.9 | 1.9 | 1.9 | 1.9 | 1.9 | 1.9 |
| Allantoin | 0.2 | 0.2 | 0.2 | 0.2 | 0.2 | 0.2 | 0.2 | 0.2 | 0.2 | 0.2 |
| Colorant | 0.12 | 0.12 | 0.12 | 0.12 | 0.12 | 0.12 | 0.12 | 0.12 | 0.12 | 0.12 |
| Water | Bal. | Bal. | Bal. | Bal. | Bal. | Bal. | Bal. | Bal. | Bal. | Bal. |
| PHASE B | | | | | | | | | | |
| Primrose Oil | 1.0 | 1.0 | 1.0 | 1.0 | 1.0 | 1.0 | 1.0 | 1.0 | 1.0 | 1.0 |
| Elefac-205 ® | 3.0 | 3.0 | 3.0 | 3.0 | 3.0 | 3.0 | 3.0 | 3.0 | 3.0 | 3.0 |
| Borage Oil | 1.0 | 1.0 | 1.0 | 1.0 | 1.0 | 1.0 | 1.0 | 1.0 | 1.0 | 1.0 |
| Tridecylsalicylate | 2.0 | 2.0 | 2.0 | 2.0 | 2.0 | 2.0 | 2.0 | 2.0 | 2.0 | 2.0 |
| Alpha-Bisabolol | 0.1 | 0.1 | 0.1 | 0.1 | 0.1 | 0.1 | 0.1 | 0.1 | 0.1 | 0.1 |
| Glyceryl Stearate | 1.0 | 1.0 | 1.0 | 1.0 | 1.0 | 1.0 | 1.0 | 1.0 | 1.0 | 1.0 |
| Cetyl Alcohol | 1.5 | 1.5 | 1.5 | 1.5 | 1.5 | 1.5 | 1.5 | 1.5 | 1.5 | 1.5 |
| Vitamin E Acetate | 0.5 | 0.5 | 0.5 | 0.5 | 0.5 | 0.5 | 0.5 | 0.5 | 0.5 | 0.5 |
| Preservatives | 0.4 | 0.4 | 0.4 | 0.4 | 0.4 | 0.4 | 0.4 | 0.4 | 0.4 | 0.4 |
| Amphisol A ® | 2.0 | 2.0 | 2.0 | 2.0 | 2.0 | 2.0 | 2.0 | 2.0 | 2.0 | 2.0 |
| PHASE C | | | | | | | | | | |
| Water | 1.8 | 1.8 | 1.8 | 1.8 | 1.8 | 1.8 | 1.8 | 1.8 | 1.8 | 1.8 |
| Triethanolamine | 1.0 | 1.0 | 1.0 | 1.0 | 1.0 | 1.0 | 1.0 | 1.0 | 1.0 | 1.0 |
| Panthenol | 0.2 | 0.2 | 0.2 | 0.2 | 0.2 | 0.2 | 0.2 | 0.2 | 0.2 | 0.2 |
| PHASE D | | | | | | | | | | |
| Cyclomethicone | 2.0 | 2.0 | 2.0 | 2.0 | 2.0 | 2.0 | 2.0 | 2.0 | 2.0 | 2.0 |
| Silicone Elastomer *7.5% Elastomer Solids in Cyclomethicone) | 25.0 | 30.0 | 15.0 | 5.0 | 30.0 | 10.0 | 25.0 | 10.0 | 5.0 | 25.0 |
| Fragrance | 0.2 | 0.2 | 0.2 | 0.2 | 0.2 | 0.2 | 0.2 | 0.2 | 0.2 | 0.2 |

EXAMPLE 11

A study was conducted to evaluate Carbopol® as a storage stability enhancer. The cosmetic composition (concentrate) of Example 1 (herein designated as Sample 1) served as a representative of the present invention. Test Samples 2 and 3 were respectively the formulation of Example 1 but without Carbopol 1382® and without silicone elastomer. These three formulations were stored for two days at 60° C.

TABLE II

| PERFORMANCE RESULTS | SAMPLE | | |
|---|---|---|---|
| | 1 | 2 | 3 |
| Stability | No separation | Separation | Separation |
| Skin Feel | Silky feel | Not silky | Not silky |
| Foam | Easy to foam from pump | Pump needs to be primed several times before foam generates | Pump needs to be primed several times before foam generates |

Based on the above results, it is evident that the presence of both the Carbomer and the silicone elastomer are required to achieve a stable product, having a nice silky skinfeel and readily foamable from a mechanical pump.

The foregoing description and examples illustrate selected embodiments of the present invention. In light thereof variations and modifications will be suggested to one skilled in the art, all of which are within the spirit and purview of this invention.

What is claimed is:

1. A foaming cosmetic product which comprises:
   (A) a container with a nozzle outlet and a foaming mechanism; and
   (B) a cosmetic composition comprising:
      (i) from about 0.001 to about 2% by weight of a crosslinked carboxyvinyl polymer;
      (ii) from about 0.1 to about 30% of a crosslinked non-emulsifying siloxane elastomer; and
      (iii) from about 1 to about 80% of a volatile polyorganosiloxane.

2. The product according to claim 1 wherein the foaming mechanism is a mechanical device with at least one mesh screen for generating foam.

3. The product according to claim 1 wherein the foaming mechanism is a propellant.

4. The product according to claim 3 wherein the propellant is selected from $C_1$–$C_3$ alkyl ether, $C_3$–$C_6$ hydrocarbon, halocarbon, carbon dioxide and mixtures thereof.

5. The product according to claim 1 wherein the siloxane elastomer is formed from a divinyl compound reacing with Si—H linkages of a polysiloxane backbone.

6. The product according to claim 1 wherein the siloxane elastomer is Vinyl Dimethicone/Methicone Cross Polymer.

7. The product according to claim 1 wherein the elastomer is Crosslinked Stearyl Methyl Dimethyl Siloxane Copolymer.

* * * * *